(12) United States Patent
Seong et al.

(10) Patent No.: US 9,733,209 B2
(45) Date of Patent: Aug. 15, 2017

(54) ORGANIC SEMICONDUCTOR ELEMENT, FABRICATION METHOD THEREOF, WOVEN AND NON-WOVEN FABRIC STRUCTURES THEREWITH, AND SEMICONDUCTOR DEVICE THEREWITH

(71) Applicant: KOREA INSTITUTE OF MACHINERY & MATERIALS, Daejeon (KR)

(72) Inventors: Dong Gi Seong, Changwon-si (KR); Kang Eun Lee, Seongnam-si (KR); Moon Kwang Um, Changwon-si (KR); Won Oh Lee, Changwon-si (KR); Jea Uk Lee, Changwon-si (KR); Byung Mun Jung, Seoul (KR); Young Seok Oh, Changwon-si (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 14/757,467

(22) Filed: Dec. 23, 2015

(65) Prior Publication Data
US 2016/0116433 A1    Apr. 28, 2016

Related U.S. Application Data

(63) Continuation of application No. PCT/KR2015/006036, filed on Jun. 15, 2015.

(30) Foreign Application Priority Data

Jun. 17, 2014 (KR) .................. 10-2014-0073192
Jun. 17, 2014 (KR) .................. 10-2014-0073215
Jun. 17, 2014 (KR) .................. 10-2014-0073231

(51) Int. Cl.
*H01L 51/05* (2006.01)
*G01N 27/414* (2006.01)
*H01L 51/10* (2006.01)

(52) U.S. Cl.
CPC ..... *G01N 27/4141* (2013.01); *H01L 51/0516* (2013.01); *H01L 51/0558* (2013.01); *H01L 51/102* (2013.01); *H01L 51/105* (2013.01)

(58) Field of Classification Search
CPC .............. H01L 51/0516; H01L 51/102; H01L 51/0558; H01L 51/105; G01N 27/4141; G01N 27/414; G01N 27/4145
See application file for complete search history.

(56) References Cited

U.S. PATENT DOCUMENTS 6,833,059 B2 * 12/2004 Kawarada ............ G01N 27/414
                                                    204/403.01
7,081,210 B2 *  7/2006 Hirai ..................... B82Y 10/00
                                                    252/62.3 Q (Continued)

FOREIGN PATENT DOCUMENTS

JP    2003-218361 A     7/2003
KR  1020040101568 A    12/2004

(Continued)

OTHER PUBLICATIONS

Korean Office Action for application No. 10-2014-0073192 dated Mar. 27, 2015.

(Continued)

*Primary Examiner* — Nikolay Yushin
(74) *Attorney, Agent, or Firm* — Hauptman Ham, LLP

(57) ABSTRACT

Disclosed are an organic semiconductor element, a fabrication method thereof, woven and non-woven fabric structures therewith, and a semiconductor device therewith. The organic semiconductor element comprising an organic semiconductor layer; a linear source electrode and a linear drain (Continued)

electrode provided in the organic semiconductor layer and spaced apart from and parallel to each other; a linear gate electrode provided on the organic semiconductor layer to cross the linear source and drain electrodes; and an electrolyte layer in contact with the organic semiconductor layer and the linear gate electrode.

13 Claims, 25 Drawing Sheets

(56) References Cited

U.S. PATENT DOCUMENTS

| 7,646,013 B2* | 1/2010 | Herlogsson | H01L 51/0516 257/40 |
|---|---|---|---|
| 2005/0148179 A1* | 7/2005 | Hirai | B82Y 10/00 438/689 |

FOREIGN PATENT DOCUMENTS

| KR | 1020050028289 A | 5/2006 |
|---|---|---|
| KR | 1020080049343 A | 6/2012 |

OTHER PUBLICATIONS

Korean Office Action for application No. 10-2014-0073215 dated Mar. 27, 2015.
Korean Office Action for application No. 10-2014-0073231 dated Mar. 31, 2015.

* cited by examiner

ORGANIC SEMICONDUCTOR ELEMENT, FABRICATION METHOD THEREOF, WOVEN AND NON-WOVEN FABRIC STRUCTURES THEREWITH, AND SEMICONDUCTOR DEVICE THEREWITH

CROSS-REFERENCE TO RELATED APPLICATIONS

This U.S. non-provisional patent application claims priority under 35 U.S.C. §119 to Korean Patent Application No. 10-2014-0073231, filed on Jun. 17, 2014, 10-2014-0073215, filed on Jun. 17, 2014, 10-2014-0073192, filed on Jun. 17, 2014, and International Application No. PCT/KR2015/006036, filed on Jun. 15, 2015, in the Korean Intellectual Property Office, the entire contents of which are hereby incorporated by reference.

BACKGROUND

1. Field

The present disclosure relates to an organic semiconductor element, a fabrication method thereof, woven and non-woven fabric structures therewith, and a semiconductor device therewith.

2. Description of the Related Art

There is an increasing interest on Organic Field Effect Transistors (OFETs) and Organic ElectroChemical Transistors (OECTs), whose active layer is formed of an organic semiconductor material. In particular, filament devices with the OFETs or OECTs are being actively studied with the aim of developing a textile device.

The fabrication process of the OFETs or OECTs may include, for example, coating a fiber with a conductive material and then partially removing the coated conductive layer to form a gap. The formation of the gap makes it possible to allow source and drain electrode patterns on each fiber to be spaced apart from each other.

SUMMARY

In order to form the source and drain electrode patterns spaced apart from each other by the gap on each fiber, it is necessary to additionally perform a process of pattering the fiber coated with the conductive layer. However, since the patterning process is a relatively-complicated and costly process, such an addition of the patterning process may lead to an increase in fabrication cost.

Also, it is necessary to develop the filament device with the OFET or OECT in such a way that a source fiber, a drain fiber, and a gate fiber thereof are efficiently arranged.

Some embodiments of the inventive concept provide an organic semiconductor element, which can be fabricated without using a patterning process, a method of fabricating an organic semiconductor element without using a patterning process, a fabrication method thereof, woven and non-woven fabric structures therewith, and a semiconductor device therewith.

Some embodiments of the inventive concept provide an organic semiconductor element that is capable of effectively serving as a filament device, a fabrication method thereof, woven and non-woven fabric structures therewith, and a semiconductor device therewith, and here, the organic semiconductor element is configured to include source, drain, and gate fibers, which are efficiently arranged.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an organic semiconductor element comprising: an organic semiconductor layer; a linear source electrode and a linear drain electrode provided in the organic semiconductor layer and spaced apart from and parallel to each other; a linear gate electrode provided on the organic semiconductor layer to cross the linear source and drain electrodes; and an electrolyte layer in contact with the organic semiconductor layer and the linear gate electrode.

In accordance with an aspect of an another exemplary embodiment, there is provided an organic semiconductor element comprising: a linear source electrode and a linear drain electrode spaced apart from and parallel to each other; an organic semiconductor layer disposed between the linear source and drain electrodes; a linear gate electrode disposed on the organic semiconductor layer to cross the linear source and drain electrodes; and an electrolyte layer in contact with the organic semiconductor layer and the linear gate electrode.

In accordance with an aspect of an exemplary embodiment, there is provided a method of fabricating an organic semiconductor element, comprising: coating a linear source electrode and a linear drain electrode, which are spaced apart from and parallel to each other, with an organic semiconductor material; disposing a linear gate electrode to cross the linear source and drain electrodes coated with the organic semiconductor material; and coating an electrolyte material on a resulting structure provided with the linear gate electrode.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

Figure 1:
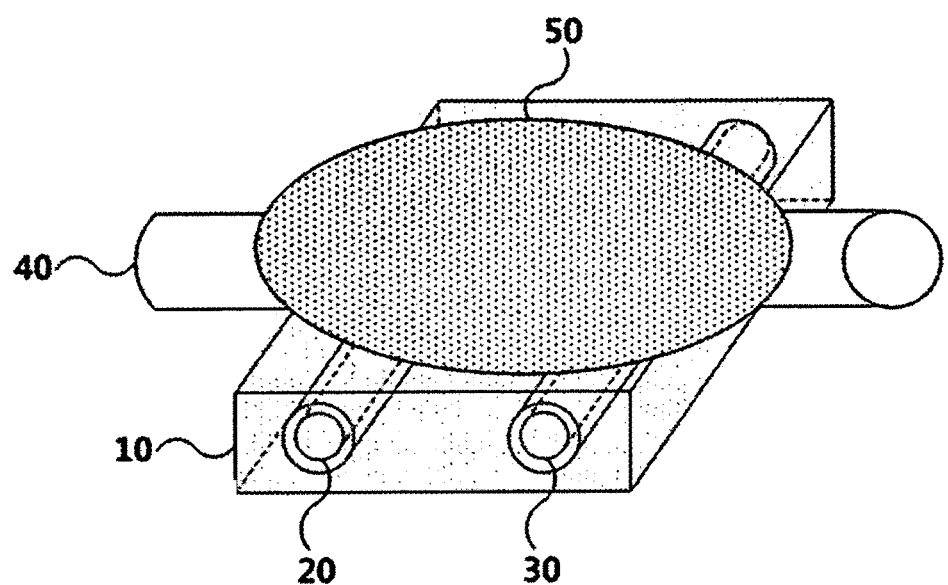
FIG. 1 is a perspective view illustrating an organic semiconductor element according to a first embodiment of the inventive concept.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Hereinafter, organic semiconductor elements according to first to fourth embodiment of the inventive concept will be described with reference to the accompanying drawings.

Firstly, an organic semiconductor element according to a first embodiment of the inventive concept will be described with reference to FIG. 1. Referring to FIG. 1, a perspective view of the organic semiconductor element according to the first embodiment of the inventive concept is illustrated.

An organic semiconductor element may include an organic semiconductor layer 10, a linear source electrode 20, a linear drain electrode 30, a linear gate electrode 40, and an electrolyte layer 50. The organic semiconductor element may be used as, for example, a sensor providing information on external environment. As an example, the sensor using the organic semiconductor element may be configured to detect a sensing-target material (e.g., an air pollution gas including carbon dioxide or harmful ultraviolet light), but the inventive concept is not limited thereto. That is, there is a sensing-target material in the external environment, the sensing-target material may lead to a change in electrical characteristics of the electrolyte layer 50, and this may make it possible to allow an electric current to flow between the linear source and drain electrodes 20 and 30 through a channel region of the organic semiconductor layer 10.

The organic semiconductor layer 10 may include an organic semiconductor material, such as pentacene or conductive polymer materials (e.g., Poly-3-Hexylthiophene (P3HT) and PEDOT:PSS), but the inventive concept is not limited thereto.

The organic semiconductor layer 10 may be provided to cover at least partially the linear source and drain electrodes 20 and 30; for example, the organic semiconductor layer 10 may be provided to enclose the linear source and drain electrodes 20 and 30. Accordingly, the linear source and drain electrodes 20 and 30 may be combined with each other by the organic semiconductor layer 10 to constitute a single assembly. At least a portion of the organic semiconductor layer 10 may be positioned between the linear source and drain electrodes 20 and 30 to serve as a channel region of the organic semiconductor element.

Furthermore, the organic semiconductor layer 10 may extend parallel to the linear source and drain electrodes 20 and 30. Thus, the organic semiconductor layer 10 may have two opposite surfaces (e.g., top and bottom surfaces) extending parallel to the linear source and drain electrodes 20 and 30. In some embodiments, the top or bottom surface of the organic semiconductor layer 10 may be a substantially flat plane, but the inventive concept is not limited thereto.

Each of the linear source and drain electrodes 20 and 30 may be a linear conductive element extending in a first direction, and the linear source and drain electrodes 20 and 30 may serve as source and drain electrodes, respectively, of the organic semiconductor element. The linear source and drain electrodes 20 and 30 may be formed of or include at least one of metallic materials (e.g., gold, silver, copper, and aluminum), conductive polymer materials, or carbon-based materials, but the inventive concept is not limited thereto. For example, each of the linear source and drain electrodes 20 and 30 may be provided in the form of a gold-containing wire or a polymer fiber coated with gold (Au) or PEDOT:PSS, but the inventive concept is not limited thereto. In other words, according to the organic semiconductor element in some embodiments of the inventive concept, it is possible to form the linear source and drain electrodes 20 and 30, without any patterning process, and this may make it possible to reduce cost and time in a fabrication process.

The linear source and drain electrodes 20 and 30 may be spaced apart from and parallel to each other and may be provided in, for example, the organic semiconductor layer 10. The linear source and drain electrodes 20 and 30 may be coated with the organic semiconductor layer 10, and thus, it is possible to maintain the parallel disposition of the linear source and drain electrodes 20 and 30. The linear source and drain electrodes 20 and 30, in conjunction with the organic semiconductor layer 10 with the channel region, may constitute an assembly of the organic semiconductor element according to some embodiments of the inventive concept.

The linear gate electrode 40 may be a linear conductive element extending in a second direction and may be formed of at least one of metallic materials (e.g., gold, silver, copper, and aluminum), conductive polymer materials, or carbon-based materials; for example, the linear gate electrode 40 may be provided in the form of an aluminum or gold containing wire, but the inventive concept is not limited thereto. In addition, the linear gate electrode 40 may be disposed on the organic semiconductor layer 10 to cross the linear source and drain electrodes 20 and 30, and the electrolyte layer 50 may be provided to fix disposition of the linear gate electrode 40 relative to the linear source and drain electrodes 20 and 30. In detail, since the extension direction (i.e., the second direction) of the linear gate electrode 40 is not parallel to the first direction, the linear gate electrode 40 may cross the linear source and drain electrodes 20 and 30 extending in the first direction. For example, the extension direction (i.e., the second direction) of the linear gate electrode 40 may be perpendicular to the first direction, but the inventive concept is not limited thereto.

The electrolyte layer 50 may be composed of an ionic liquid electrolyte, a solid electrolyte, or a mixture thereof, but the inventive concept is not limited thereto. Also, the electrolyte layer 50 may be formed by blending 1-Butyl-2, 3-dimethylimidazolium Bis(trifluoromethanesulfonyl)imde ([EMIM][Ntf2]) and poly(vinylidene fluoride)-hexafluoroprophlene (PVDF-HFP) or blending Nafion and poly(vinyl alcohol), but the inventive concept is not limited thereto.

The electrolyte layer 50 may be provided to be in contact with the organic semiconductor layer 10 and the linear gate electrode 40; for example, the linear gate electrode 40 may be attached to the linear source and drain electrodes 20 and 30, which are coated with the organic semiconductor layer 10, by the electrolyte layer 50. As an example, the electrolyte layer 50 may include at least a portion interposed between the organic semiconductor layer 10 and the linear gate electrode 40. Furthermore, the electrolyte layer 50 may cover not only the top surface of the organic semiconductor layer 10 but also the linear gate electrode 40 thereon, but the inventive concept is not limited thereto.

The organic semiconductor element according to some embodiments of the inventive concept may be a planar-type OECT device and may be used as a monofilament. In particular, since the linear source and drain electrodes 20 and 30 are formed without using a patterning process, it is possible to reduce fabrication cost and time.

Figure 2:
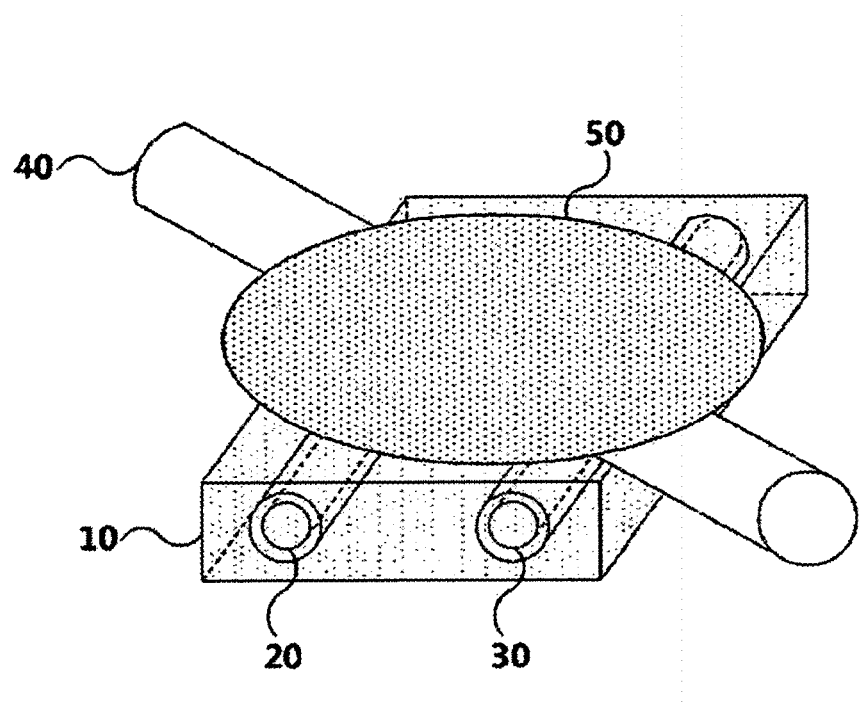
FIG. 2 is a perspective view illustrating an organic semiconductor element according to a second embodiment of the inventive concept.

An organic semiconductor element according to second embodiment of the inventive concept will be described with reference to FIG. 2. For concise description, the following description will mainly refer to an element or feature that is different from that in the first embodiment or is not described therein, whereas a previously described element will be identified by a similar or identical reference number without repeating an overlapping description thereof. Referring to FIG. 2, a perspective view of the organic semiconductor element according to the second embodiment of the inventive concept is illustrated.

As shown in FIG. 2, the linear gate electrode 40 may be disposed on the organic semiconductor layer 10 to cross the linear source and drain electrodes 20 and 30, and the electrolyte layer 50 may be provided to fix such a disposition of the linear gate electrode 40 relative to the linear source and drain electrodes 20 and 30. Here, the extension direction (i.e., the second direction) of the linear gate electrode 40 may not be parallel to the first direction, and in this case, the linear gate electrode 40 may cross the linear source and drain electrodes 20 and 30 extending in the first direction. However, the extension direction (i.e., the second direction) of the linear gate electrode 40 may not be perpendicular to the first direction.

Figure 3:
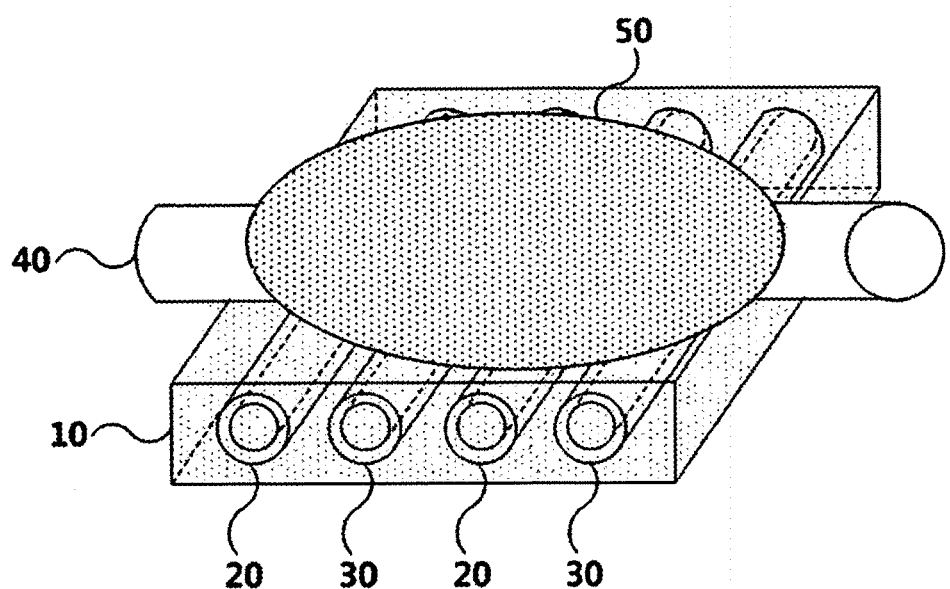
FIG. 3 is a perspective view illustrating an organic semiconductor element according to a third embodiment of the inventive concept.

An organic semiconductor element according to a third embodiment of the inventive concept will be described with reference to FIG. 3. For concise description, the following description will mainly refer to an element or feature that is different from that in the first embodiment or is not described therein, whereas a previously described element will be identified by a similar or identical reference number without repeating an overlapping description thereof. Referring to FIG. 3, a perspective view of the organic semiconductor element according to the third embodiment of the inventive concept is illustrated.

As shown in FIG. 3, a plurality of linear source electrodes 20 and a plurality of linear drain electrodes 30 may be provided. The linear source electrodes 20 and the linear drain electrodes 30 may be arranged one by one in an alternate manner, thereby forming an array. For example, the plurality of linear source electrodes 20 and the plurality of linear drain electrodes 30 may extend in the first direction, whereas the linear gate electrode 40 may extend in the second direction that is not parallel to the first direction. In this case, the plurality of linear source electrodes 20 and the plurality of linear drain electrodes 30 may be arranged one by one in an alternate manner in the extension direction (e.g., the second direction) of the linear gate electrode 40.

Figure 4:
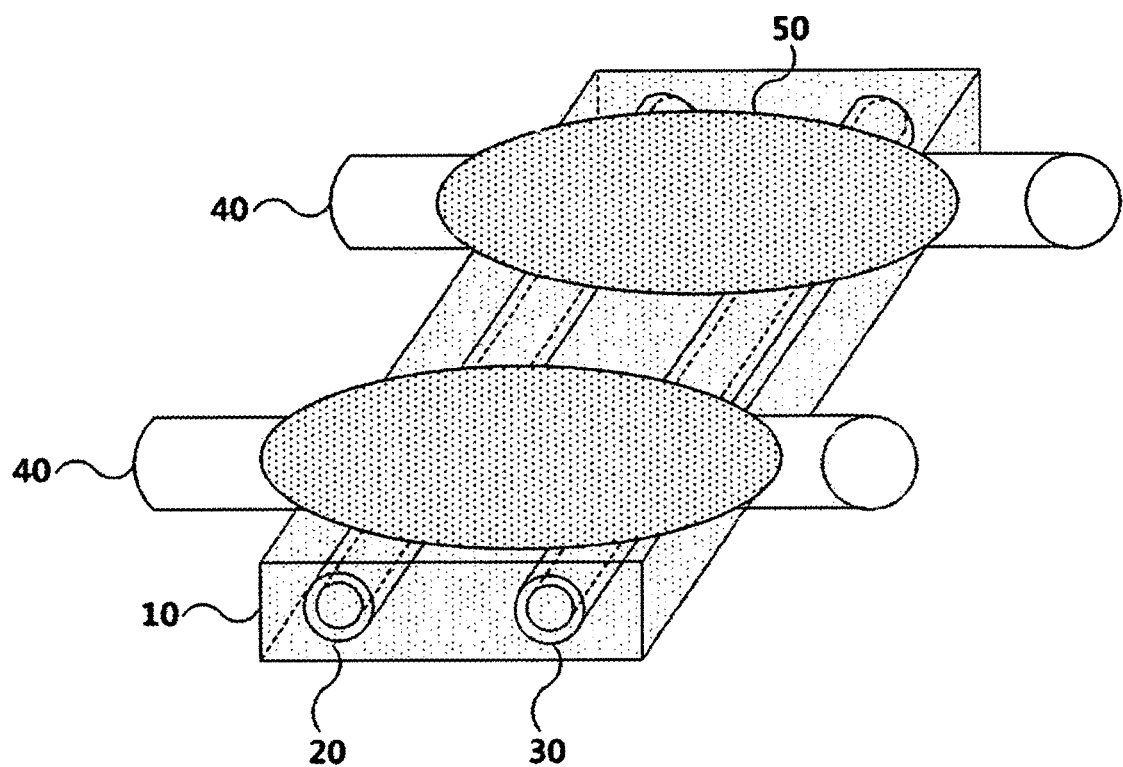
FIG. 4 is a perspective view illustrating an organic semiconductor element according to a fourth embodiment of the inventive concept.

An organic semiconductor element according to a fourth embodiment of the inventive concept will be described with reference to FIG. 4. For concise description, the following description will mainly refer to an element or feature that is different from that in the first embodiment or is not described therein, whereas a previously described element will be identified by a similar or identical reference number without repeating an overlapping description thereof. Referring to FIG. 4, a perspective view of the organic semiconductor element according to the fourth embodiment of the inventive concept is illustrated.

As shown in FIG. 4, a plurality of linear gate electrodes 40 may be provided. The plurality of linear gate electrodes 40 may be disposed to be spaced apart from and parallel to each other. Furthermore, the plurality of linear gate electrodes 40 maybe disposed on the organic semiconductor layer 10 to cross the linear source and drain electrodes 20 and 30. In certain embodiments, the electrolyte layer 50 may include a plurality of parts that are separated from each other, and each of the linear gate electrodes 40 may be attached to the organic semiconductor layer 10 using a corresponding one of the separate parts of the electrolyte layer 50.

Hereinafter, methods of fabricating the organic semiconductor elements according to the first to fourth embodiment of the inventive concept will be described with reference to FIGS. 5 through 10.

Figure 5:
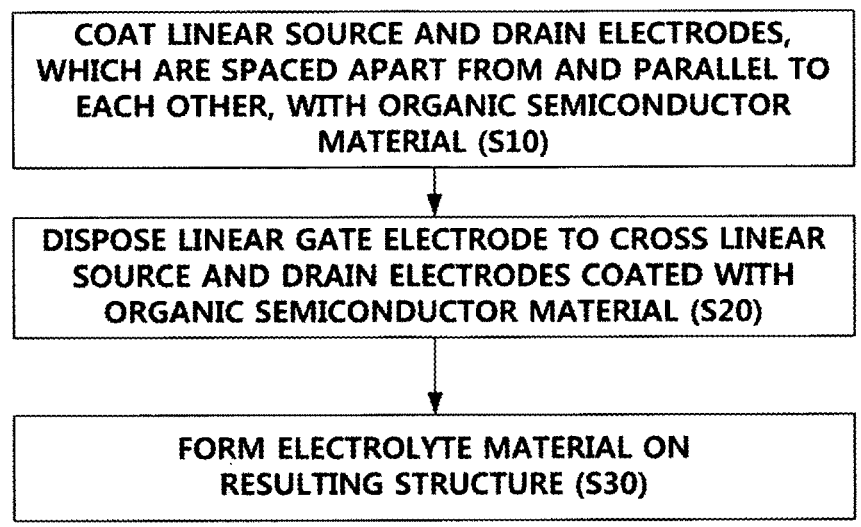
FIG. 5 is a flow chart illustrating a method of fabricating an organic semiconductor element, according to the first to fourth embodiments of the inventive concept.
Figure 9:
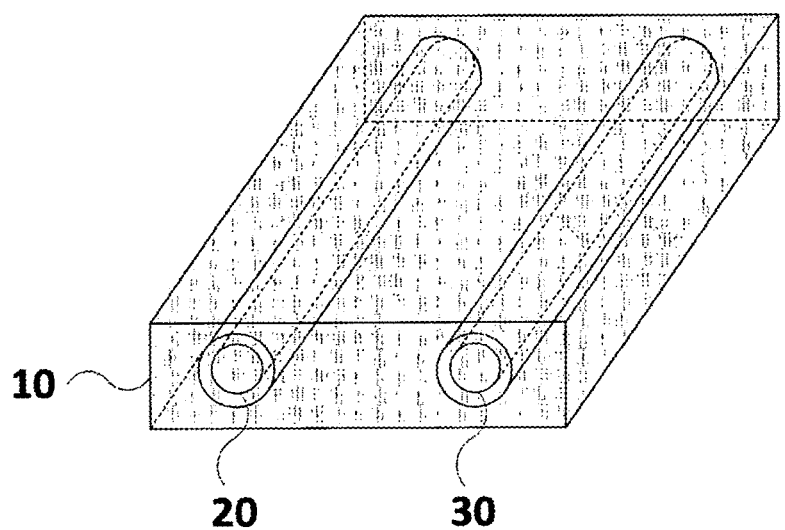

Firstly, referring to FIGS. 5 and 9, the linear source and drain electrodes 20 and 30 may be arranged spaced apart from and parallel to each other and then may be coated with an organic semiconductor material, in operation S10.

For example, the organic semiconductor material may be simultaneously coated on the linear source and drain electrodes 20 and 30, and this may make it possible to maintain the parallel separation between the linear source and drain electrodes 20 and 30. There may be several methods allowing for the parallel separation between the linear source and drain electrodes 20 and 30, and the inventive concept is not limited to a specific one of such methods.

The operation S10 may include several operations S11, S12, and S13. For example, referring to FIGS. 6 and 7, the linear source and drain electrodes 20 and 30 may be prepared, and then, the linear source and drain electrodes 20 and 30 may be preliminarily coated with an organic semiconductor material, before coating the linear source and drain electrodes 20 and 30 with an organic semiconductor material, in operation S11.

The linear source and drain electrodes 20 and 30 may be gold-containing wires and may be formed by, for example, a gold evaporation process, a dip-coating process or a vertical-dropping process. The gold evaporation process may be performed in such a way that gold is evaporated to form a gold layer of about 100 nm thickness on a polymer fiber of about 500 um diameter. The dip-coating process or the vertical-dropping process may be performed in such a way that PEDOT:PSS added with 5% diethylene glycol and 0.1% zonyl is formed to have a thickness of about 300 nm on a polymer fiber of about 500 um diameter.

The preliminary coating on the linear source and drain electrodes 20 and 30 may be performed by, for example, depositing a pentacene layer of about 100 nm thickness on the linear source and drain electrodes 20 and 30 using an evaporation process, depositing a P3HT layer of about 100 nm thickness on the linear source and drain electrodes 20 and 30 using a dip coating process, or depositing a PEDOT:PSS layer of about 100 nm thickness on the linear source and drain electrodes 20 and 30 using a dip coating process, but the inventive concept is not limited thereto.

Figure 6:
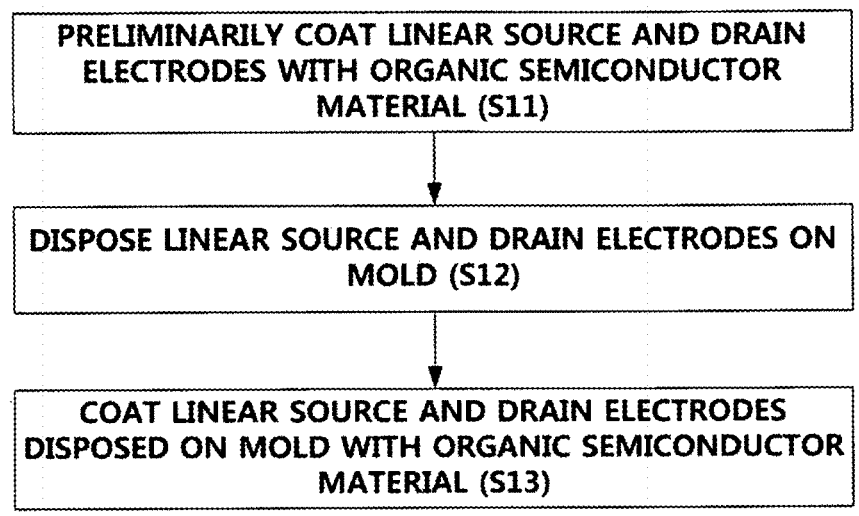
FIG. 6 is a flow chart provided to describe the operation S10 of FIG. 5 in more detail.
Figure 7:
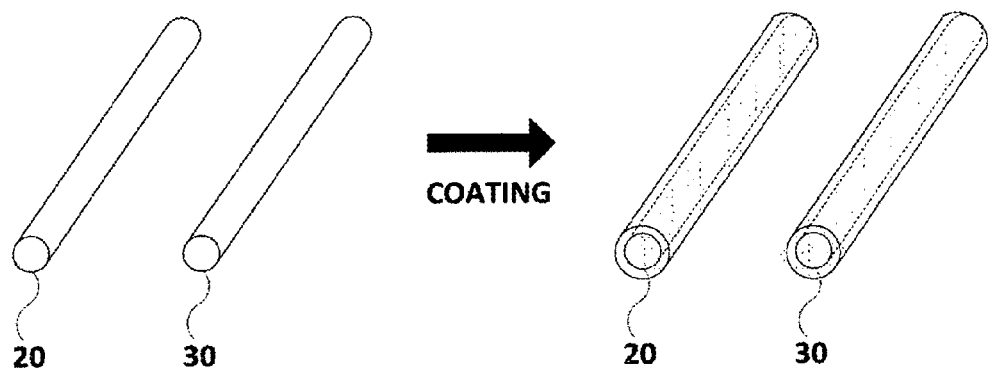
FIGS. 7 through 10 are perspective views illustrating a method of fabricating an organic semiconductor element, according to the first to fourth embodiments of the inventive concept.
Figure 8:
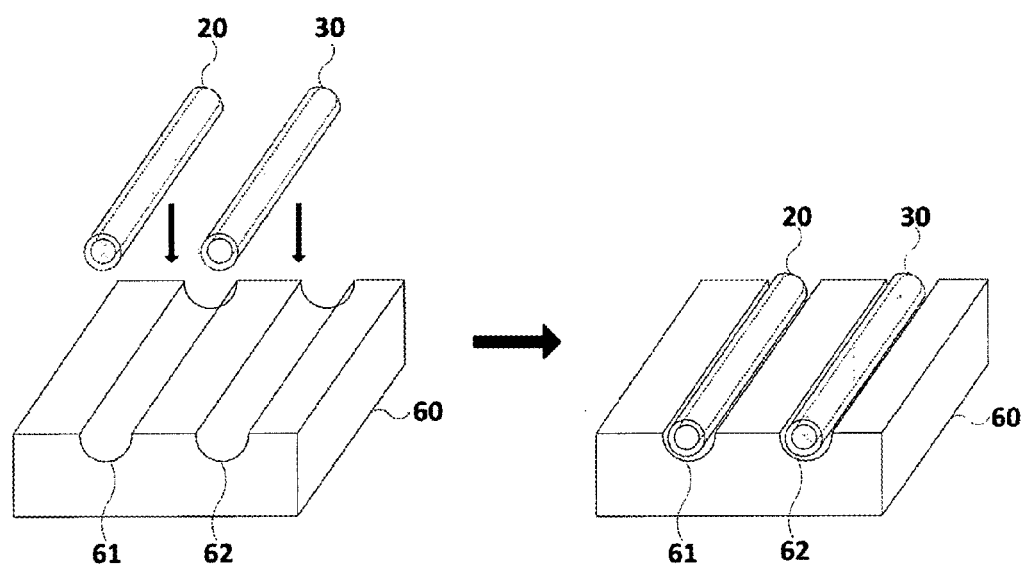

Thereafter, referring to FIGS. 6 and 8, the linear source and drain electrodes 20 and 30 may be disposed on first and second grooves 61 and 62, respectively, of a mold 60, in operation S12. The first and second grooves 61 and 62 may be provided parallel to each other to extend in the first direction.

The mold 60 may be used to dispose the linear source and drain electrodes 20 and 30, on which the preliminary coating has been performed, in such a way that they are spaced apart from and parallel to each other. In order to realize such an arrangement of the linear source and drain electrodes 20 and 30, on which the preliminary coating has been performed, the mold 60 may include the first and second grooves 61 and 62, which are formed parallel to each other and extend in the first direction, and in this case, a channel length of the organic semiconductor element may be given by a spaced distance (e.g., 100 um) between the first groove 61 and the second groove 62, although the inventive concept is not limited thereto.

By disposing the linear source and drain electrodes 20 and 30 in the first and second grooves 61 and 62 of the mold 60, it is possible to maintain the parallel separation between the linear source and drain electrodes 20 and 30.

Next, referring to FIGS. 6 and 9, the linear source and drain electrodes 20 and 30, which are respectively disposed in the first and second grooves 61 and 62, may be coated with an organic semiconductor material, in operation S13.

The operation S13 of coating the linear source and drain electrodes 20 and 30 with the organic semiconductor material may be performed in substantially the same manner as the preliminary coating. However, since the linear source and drain electrodes 20 and 30 are respectively disposed in the first and second grooves 61 and 62, it is possible to coat the linear source and drain electrodes 20 and 30 with the organic semiconductor material, while maintaining the parallel separation therebetween. As a result, the linear source and drain electrodes 20 and 30 may be disposed in the organic semiconductor layer 10.

Figure 10:
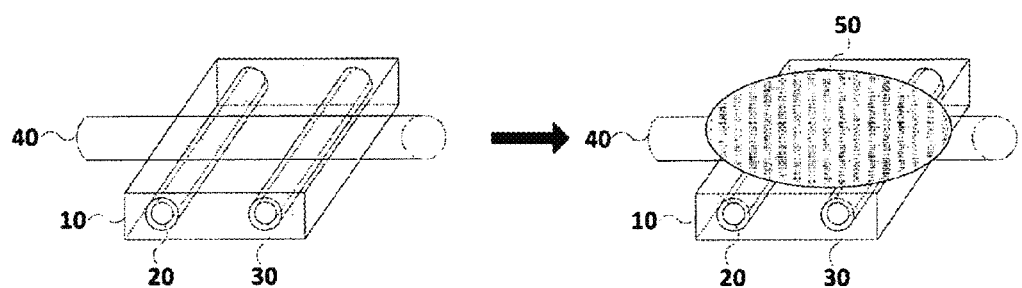

Thereafter, referring to FIGS. 5 and 10, the linear gate electrode 40 may be disposed on the linear source and drain electrodes 20 and 30, which are covered with the organic semiconductor layer 10, to cross the linear source and drain electrodes 20 and 30, in operation S20.

For example, the linear gate electrode 40 may be an aluminum or gold-containing wire. The linear gate electrode 40 may be disposed on the linear source and drain electrodes 20 and 30, which are covered with the organic semiconductor layer 10, to cross the linear source and drain electrodes 20 and 30 and may be disposed on the organic semiconductor layer 10.

Next, referring to FIGS. 5 and 10, an electrolyte material may be coated on the resulting structure, in operation S30.

The electrolyte material may be an ionic liquid electrolyte or a solid electrolyte and may be formed by blending 1-Butyl-2,3-dimethylimidazolium Bis(trifluoromethanesulfonyl)imde ([EMIM][Ntf2]) and poly(vinylidene fluoride)-hexafluoroprophlene (PVDF-HFP) or by blending Nafion and poly(vinyl alcohol). And, the linear gate electrode 40 may be fixedly attached on the organic semiconductor layer 10 by dropping the electrolyte material on the resulting structure including the organic semiconductor layer 10, in which the linear source and drain electrodes 20 and 30 are provided, and the linear gate electrode 40.

Hereinafter, organic semiconductor elements according to fifth to seventh embodiment of the inventive concept will be described with reference to the accompanying drawings.

Figure 11:
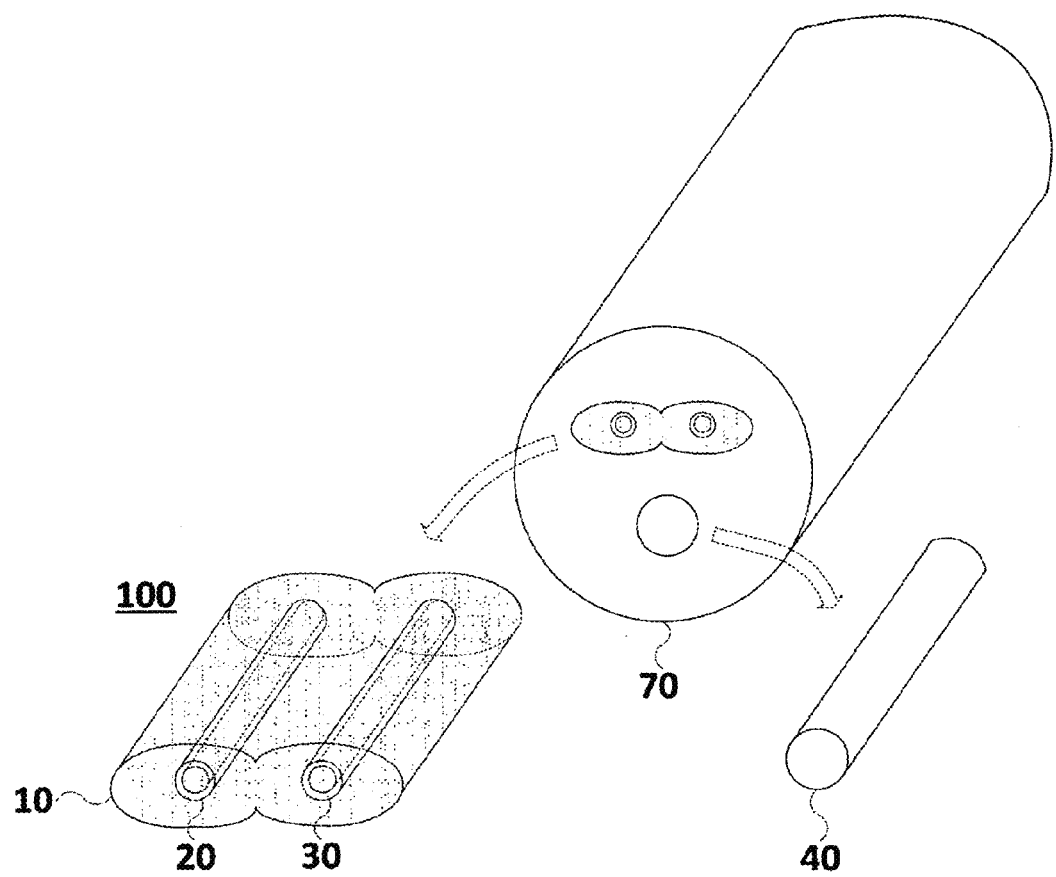
FIG. 11 is a perspective view illustrating an organic semiconductor element according to a fifth embodiment of the inventive concept.

An organic semiconductor element according to fifth embodiment of the inventive concept will be described with reference to FIG. 11. Referring to FIG. 11, a perspective view of the organic semiconductor element according to the fifth embodiment of the inventive concept is illustrated.

The organic semiconductor element may include the organic semiconductor layer 10, the linear source electrode 20, the linear drain electrode 30, the linear gate electrode 40 and a cover layer 70. The organic semiconductor element may be used as a sensor providing information on external environment; for example, the sensor using the organic semiconductor element may be used to detect a sensing-target material (e.g., an air pollution gas including carbon dioxide or harmful ultraviolet light), but the inventive concept is not limited thereto. For example, in the case where the organic semiconductor element of OFET type is used to detect a sensing-target material in the external environment, the presence of the sensing-target material may lead to a change in electrical characteristics of the organic semiconductor layer 10, and similarly, in the case where the organic semiconductor element of OECT type is used to detect a sensing-target material in the external environment, the presence of the sensing-target material may lead to a change in electrical characteristics of the cover layer 70 containing the electrolyte material. Such a change in the electrical characteristics of the organic semiconductor layer 10 or the cover layer 70 may lead to a change in amount or density of an electric current flowing through a channel region of the organic semiconductor layer 10 between the linear source electrode 20 and the linear drain electrode 30.

The organic semiconductor layer 10 may include an organic semiconductor material, such as pentacene or conductive polymer materials (e.g., Poly-3-Hexylthiophene (P3HT) and PEDOT:PSS), but the inventive concept is not limited thereto.

The organic semiconductor layer 10 may be provided in the cover layer 70 and may cover at least a portion of the linear source and drain electrodes 20 and 30. For example, the organic semiconductor layer 10 may be provided to enclose the linear source and drain electrodes 20 and 30. Accordingly, the linear source and drain electrodes 20 and 30 may be combined with each other by the organic semiconductor layer 10 to constitute a single assembly. For example, at least one linear source electrode 20 and at least one linear drain electrode 30 may be enclosed by the organic semiconductor layer 10, thereby constituting an organic assembly. The organic semiconductor layer 10 may include at least a portion, which is positioned between the linear source and drain electrodes 20 and 30 to serve as a channel region of the organic semiconductor element.

Furthermore, the organic semiconductor layer 10 may extend parallel to the linear source and drain electrodes 20 and 30 and may have two opposite surfaces, which extend parallel to the linear source and drain electrodes 20 and 30, and one of which faces the linear gate electrode 40. At least one of the opposite surfaces of the organic semiconductor layer 10 may be, for example, a plane, but the inventive concept is not limited thereto.

In the cover layer 70, each of the linear source and drain electrodes 20 and 30 may be a linear conductive element extending in a first direction, and the linear source and drain electrodes 20 and 30 may serve as source and drain electrodes, respectively, of the organic semiconductor element. The linear source and drain electrodes 20 and 30 may be formed of or include at least one of metallic materials (e.g., gold, silver, copper, and aluminum), conductive polymer materials, or carbon-based materials, but the inventive concept is not limited thereto. For example, each of the linear source and drain electrodes 20 and 30 may be provided in the form of a gold-containing wire or a polymer fiber coated with gold (Au) or PEDOT:PSS, but the inventive concept is not limited thereto. In other words, according to the organic semiconductor element in some embodiments of the inventive concept, it is possible to form the linear source and drain electrodes 20 and 30, without any patterning process, and this may make it possible to reduce cost and time in a fabrication process.

The linear source and drain electrodes 20 and 30 may be spaced apart from and parallel to each other and may be provided in, for example, the organic semiconductor layer 10. The linear source and drain electrodes 20 and 30 may be coated with the organic semiconductor layer 10, and thus, it is possible to maintain the parallel disposition of the linear source and drain electrodes 20 and 30. The linear source and drain electrodes 20 and 30, in conjunction with the organic semiconductor layer 10 with the channel region, may constitute an organic assembly 100 of the organic semiconductor element according to some embodiments of the inventive concept.

The linear gate electrode 40 may be a linear conductive element, which is provided in the cover layer 70 to extend in the first direction, and may be formed of at least one of metallic materials (e.g., gold, silver, copper, and aluminum), conductive polymer materials, or carbon-based materials; for example, the linear gate electrode 40 may be provided in the form of an aluminum or gold containing wire, but the inventive concept is not limited thereto. In addition, the linear gate electrode 40 and the linear source and drain electrodes 20 and 30 may be provided to be spaced apart from and parallel to each other, and the parallel disposition of the linear gate, source, and drain electrodes 40, 20, and 30 may be fixedly maintained by the cover layer 70.

Furthermore, the linear gate electrode 40 may be disposed spaced apart from the organic semiconductor layer 10, and at least a portion of the cover layer 70 may be provided between the linear gate electrode 40 and the organic semiconductor layer 10.

The cover layer 70 may extend in the first direction, and the organic semiconductor layer 10, the linear source electrode 20, the linear drain electrode 30 and the linear gate electrode 40 may be provided in the cover layer 70. That is, the cover layer 50 may make it possible to maintain the parallel separation between the linear source electrode 20, the linear drain electrode 30, and the linear gate electrode 40.

The cover layer 70 may contain one of electrolyte and dielectric materials. In the case where the cover layer 70 contains an electrolyte material, the organic semiconductor element may be an OECT device, and in the case where the cover layer 70 contains a dielectric material, the organic semiconductor element may be an OFET device.

In the case where the cover layer 70 contains an electrolyte material, an external sensing-target material may affect the cover layer 70. The electrolyte material may be composed of, for example, an ionic liquid electrolyte, a solid electrolyte, or a mixture thereof, but the inventive concept is not limited thereto. Also, the cover layer 70 may be formed by blending 1-Butyl-2,3-dimethylimidazolium Bis(trifluoromethanesulfonyl)imde ([EMIM][Ntf2]) and poly(vinylidene fluoride)-hexafluoroprophlene (PVDF-HFP) or blending Nafion and poly(vinyl alcohol), but the inventive concept is not limited thereto.

In the case where the cover layer 70 contains a dielectric material, an external sensing-target material may affect the organic semiconductor layer 10 or electrical characteristics thereof. Although the organic semiconductor layer 10 is provided in the cover layer 70, the external sensing-target material may pass through the cover layer 50 to reach the organic semiconductor layer 10.

The organic semiconductor element, according to some embodiments of the inventive concept, may be a circular type OECT device or a circular type OFET device and may serve as a monofilament. In particular, since the linear source and drain electrodes 20 and 30 are formed without using a patterning process, it is possible to reduce fabrication cost and time.

Figure 12:
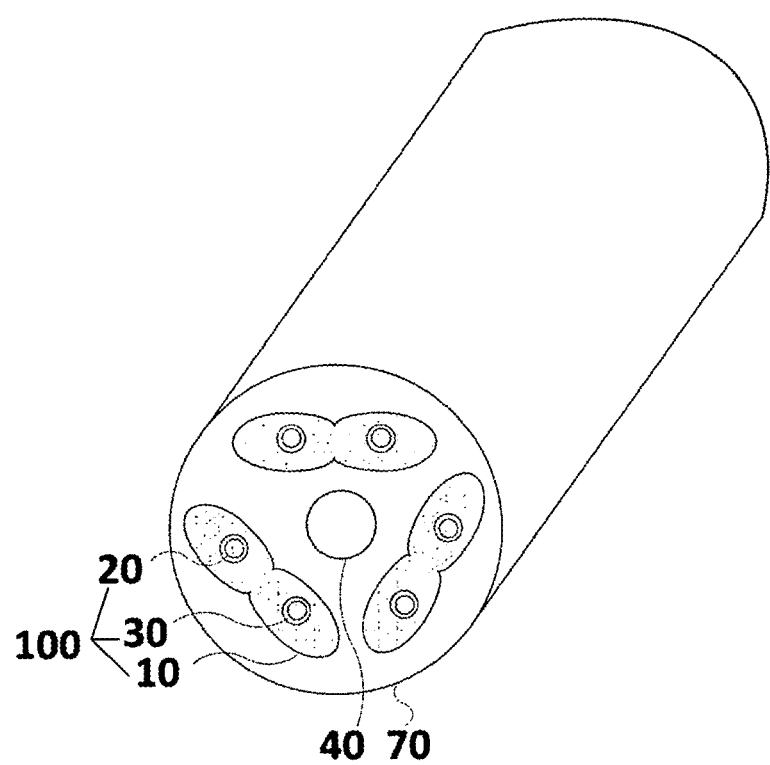
FIG. 12 is a perspective view illustrating an organic semiconductor element according to a sixth embodiment of the inventive concept.

An organic semiconductor element according to a sixth embodiment of the inventive concept will be described with reference to FIG. 12. For concise description, the following description will mainly refer to an element or feature that is different from that in the fifth embodiment or is not described therein, whereas a previously described element will be identified by a similar or identical reference number without repeating an overlapping description thereof. Referring to FIG. 12, a perspective view of the organic semiconductor element according to the sixth embodiment of the inventive concept is illustrated.

Referring to FIG. 12, an organic semiconductor element may include a plurality of the linear source electrodes 20, a plurality of the linear drain electrodes 30, and the linear gate electrode 40. In some embodiments, the organic semiconductor element may include a plurality of organic assemblies 100, which are disposed around and parallel to the linear gate electrode 40 and are spaced apart from each other. Here, each of the organic assemblies 100 may include one linear source electrode 20 and one liner drain electrode 30, and the organic semiconductor layer 10 enclosing them.

Figure 13:
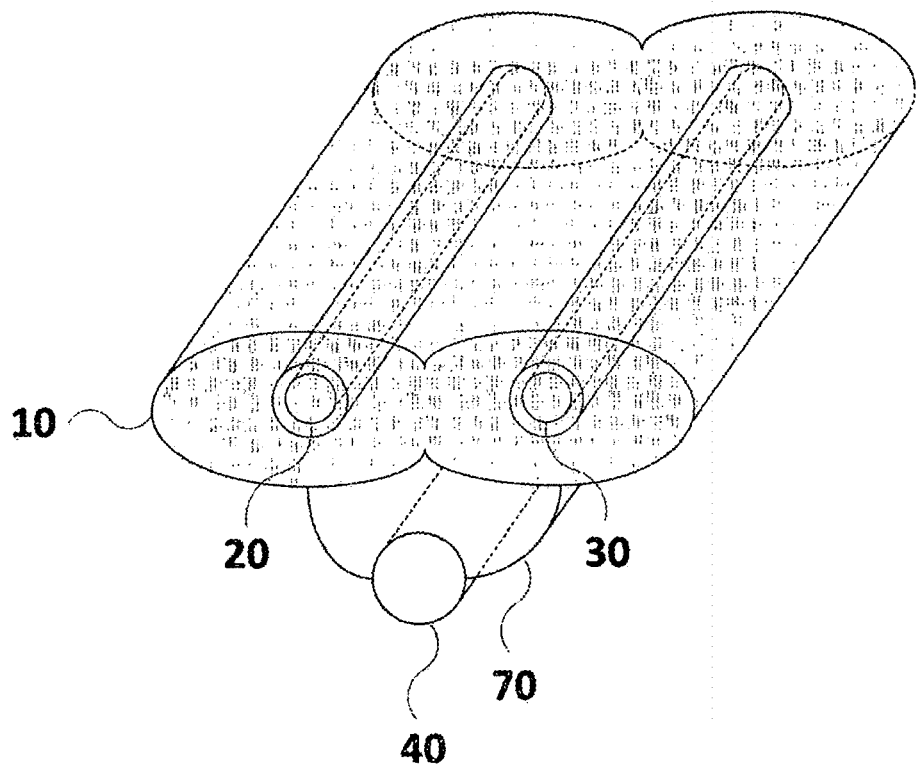
FIG. 13 is a perspective view illustrating an organic semiconductor element according to a seventh embodiment of the inventive concept.

An organic semiconductor element according to a seventh embodiment of the inventive concept will be described with reference to FIG. 13. For concise description, the following description will mainly refer to an element or feature that is different from that in the fifth embodiment or is not described therein, whereas a previously described element will be identified by a similar or identical reference number without repeating an overlapping description thereof. Referring to FIG. 13, a perspective view of the organic semiconductor element according to the seventh embodiment of the inventive concept is illustrated.

The cover layer 70 may be in contact with the organic semiconductor layer 10 and the linear gate electrode 40; for example, the linear gate electrode 40 may be attached to the linear source and drain electrodes 20 and 30, which are coated with the organic semiconductor layer 10, by the cover layer 70. As an example, the cover layer 70 may include at least a portion interposed between the organic semiconductor layer 10 and the linear gate electrode 40. Furthermore, the cover layer 70 may cover not only the top surface of the organic semiconductor layer 10 but also the linear gate electrode 40 on the top surface of the organic semiconductor layer 10, but the inventive concept is not limited thereto.

In the case of the organic semiconductor element according to the present embodiment, since the organic semiconductor layer 10 is not completely covered with the cover layer 70 and includes at least a portion exposed to the outside, an external sensing-target material may effectively affect the organic semiconductor layer 10, even when the organic semiconductor element is the OFET device.

Hereinafter, methods of fabricating an organic semiconductor element, according to fifth to seventh embodiments of the inventive concept, will be described with reference to FIGS. 14 through 19. In detail, FIG. 14 is a flow chart illustrating methods of fabricating organic semiconductor elements according to the fifth to seventh embodiment of the inventive concept, FIG. 15 is a flow chart illustrating operation S110 of FIG. 14, and FIGS. 16 through 19 are perspective views illustrating methods of fabricating an organic semiconductor element, according to the fifth to seventh embodiments of the inventive concept.

Figure 14:
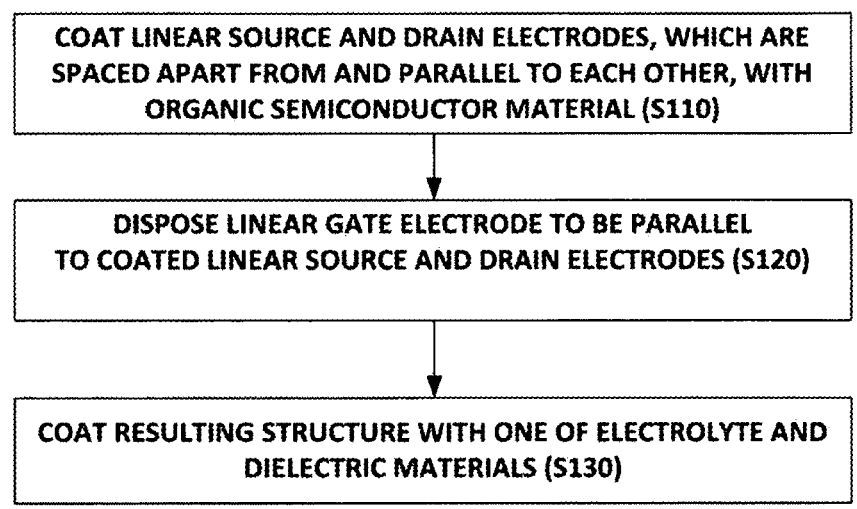
FIG. 14 is a flow chart illustrating a method of fabricating an organic semiconductor element, according to the fifth to seventh embodiments of the inventive concept.
Figure 15:
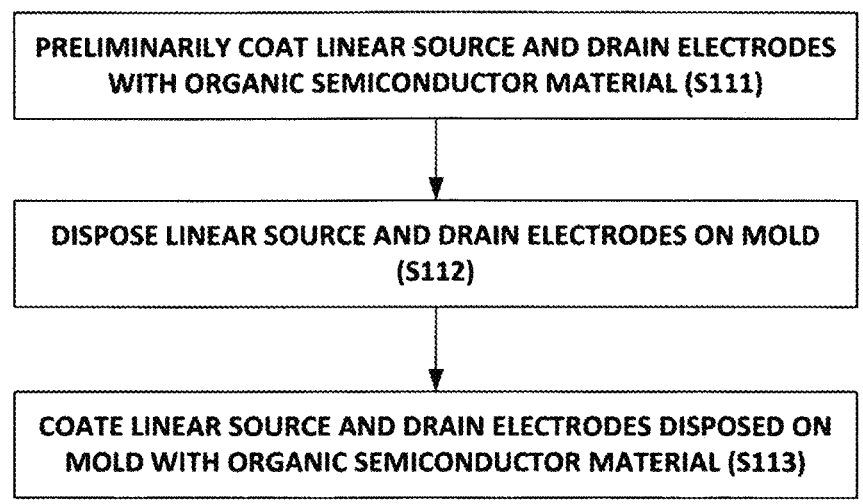
FIG. 15 is a flow chart provided to describe the operation S110 of FIG. 14 in more detail.
Figure 16:
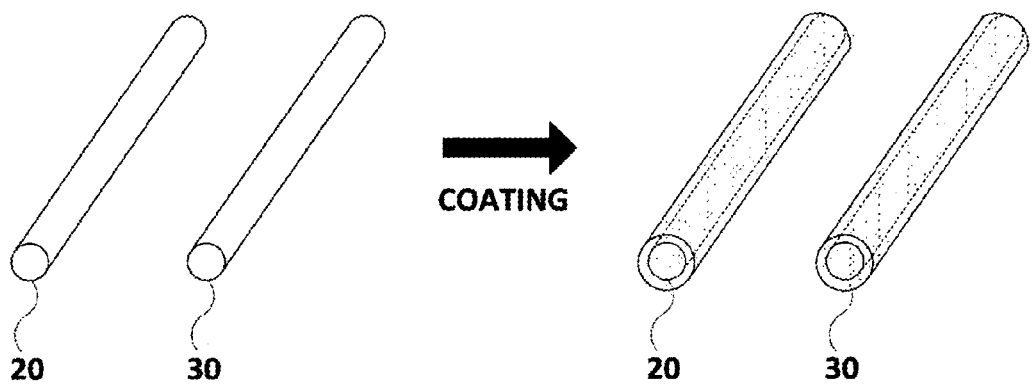
FIGS. 16 through 19 are perspective views illustrating a method of fabricating an organic semiconductor element, according to the fifth to seventh embodiments of the inventive concept.
Figure 18:
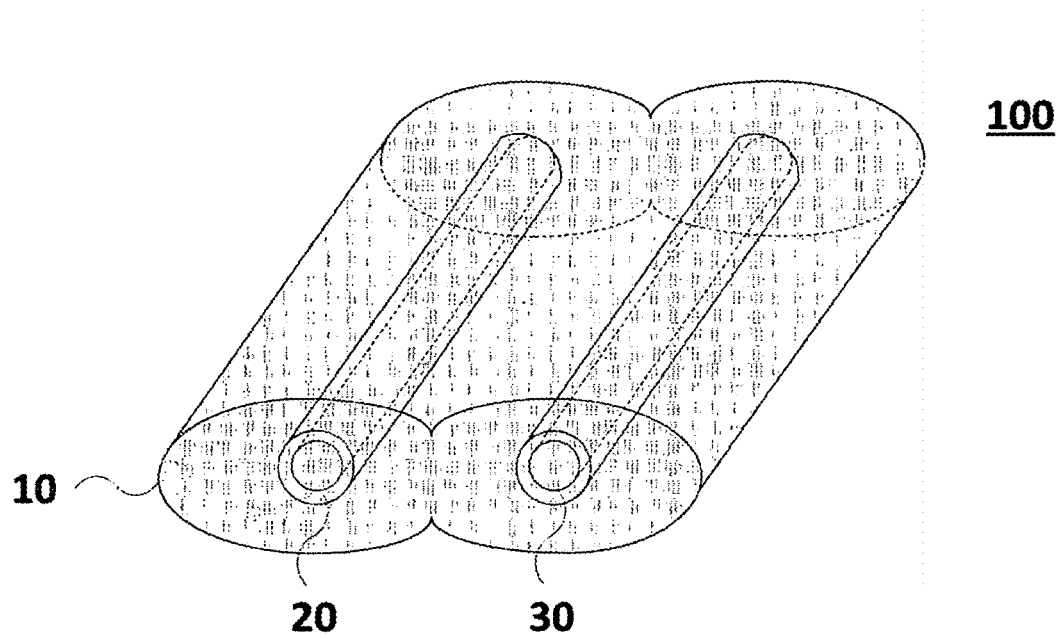

Firstly, referring to FIGS. 14 and 18, the linear source and drain electrodes 20 and 30 may be arranged spaced apart from and parallel to each other and then may be coated with an organic semiconductor material, in operation S110.

For example, the organic semiconductor material may be simultaneously coated on the linear source and drain electrodes 20 and 30, and this may make it possible to maintain the parallel separation between the linear source and drain electrodes 20 and 30. There may be several methods allowing for the parallel separation between the linear source and drain electrodes 20 and 30, and the inventive concept is not limited to a specific one of such methods.

The operation S110 may include several operations S111, S112, and S113. For example, referring to FIGS. 15 and 16, the linear source and drain electrodes 20 and 30 may be prepared, and then, the linear source and drain electrodes 20 and 30 may be preliminarily coated with an organic semiconductor material, before coating the linear source and drain electrodes 20 and 30 with an organic semiconductor material, in operation S111.

The linear source and drain electrodes 20 and 30 may be gold-containing wires and may be formed by, for example, a gold evaporation process, a dip-coating process or a vertical-dropping process. The gold evaporation process may be performed in such a way that gold is evaporated to form a gold layer of about 100 nm thickness on a polymer fiber of about 500 um diameter. The dip-coating vertical-dropping process may be performed in such a way that PEDOT:PSS added with 5% diethylene glycol and 0.1% zonyl is formed to have a thickness of about 300 nm on a polymer fiber of about 500 um diameter.

The preliminary coating on the linear source and drain electrodes 20 and 30 may be performed by, for example, depositing a pentacene layer of about 100 nm thickness on the linear source and drain electrodes 20 and 30 using an evaporation process, depositing a P3HT layer of about 100 nm thickness on the linear source and drain electrodes 20 and 30 using a dip coating process, or depositing a PEDOT:PSS layer of about 100 nm thickness on the linear source and drain electrodes 20 and 30 using a dip coating process, but the inventive concept is not limited thereto.

Figure 17:
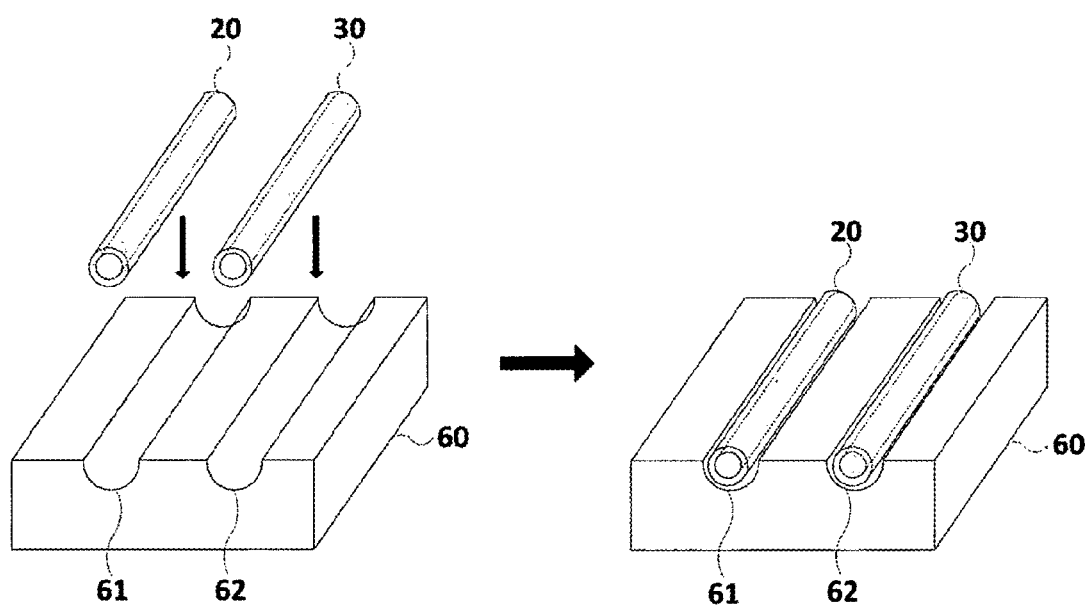

Thereafter, referring to FIGS. 15 and 17, the linear source and drain electrodes 20 and 30 may be disposed on the first and second grooves 61 and 62, respectively, of the mold 60, in operation S112. Here, the first and second grooves 61 and 62 of the mold 60 may be formed to extend in the first direction and be parallel to each other.

The mold 60 may be used to dispose the linear source and drain electrodes 20 and 30, on which the preliminary coating has been performed, in such a way that they are spaced apart from and parallel to each other. In order to realize such an arrangement of the linear source and drain electrodes 20 and 30, on which the preliminary coating has been performed, the mold 60 may include the first and second grooves 61 and 62, which are formed parallel to each other and extend in the first direction, and in this case, a channel length of the organic semiconductor element may be given by a spaced distance (e.g., 100 um) between the first groove 61 and the second groove 62, although the inventive concept is not limited thereto.

By disposing the linear source and drain electrodes 20 and 30 in the first and second grooves 61 and 62 of the mold 60, it is possible to maintain the parallel separation between the linear source and drain electrodes 20 and 30.

Next, referring to FIGS. 15 and 18, the linear source and drain electrodes 20 and 30, which are respectively disposed in the first and second grooves 61 and 62, may be coated with an organic semiconductor material, in operation S113.

The operation S113 of coating the linear source and drain electrodes 20 and 30 with the organic semiconductor material may be performed in substantially the same manner as the preliminary coating. However, since the linear source and drain electrodes 20 and 30 are respectively disposed in the first and second grooves 61 and 62, it is possible to coat the linear source and drain electrodes 20 and 30 with the organic semiconductor material, while maintaining the parallel separation therebetween. As a result, the linear source and drain electrodes 20 and 30 may be disposed in the organic semiconductor layer 10.

Figure 19:
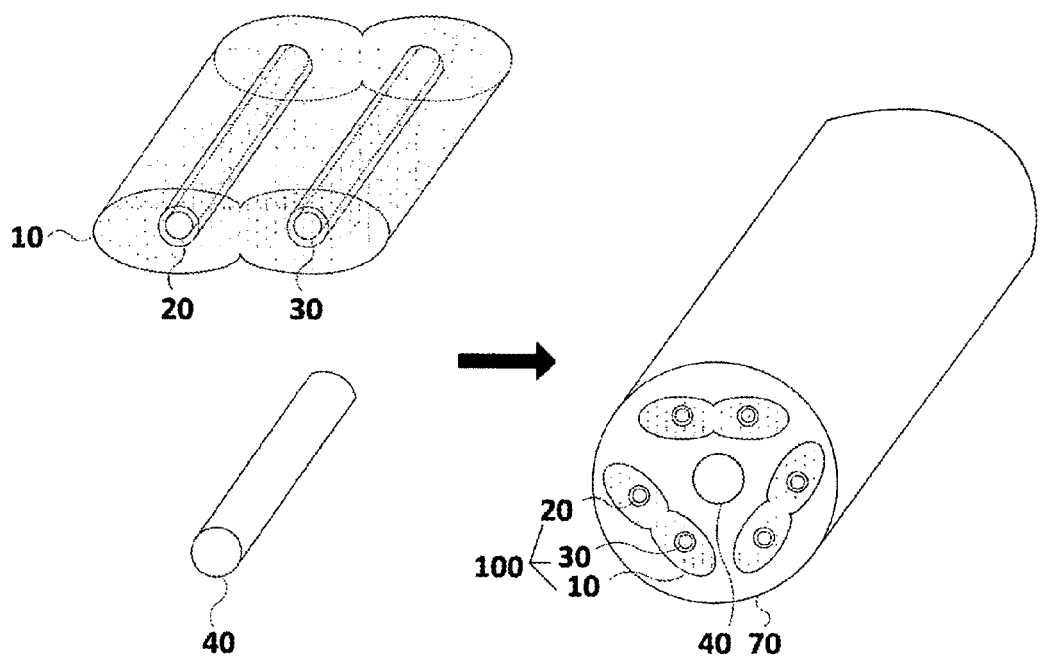

Thereafter, referring to FIGS. 14 and 19, the linear gate electrode 40 may be disposed to be parallel to the linear source and drain electrodes 20 and 30 coated with the organic semiconductor material, in operation S120.

For example, the linear gate electrode 40 may be an aluminum or gold-containing wire. The linear gate electrode 40 may be disposed to be parallel to the linear source and drain electrodes 20 and 30.

Thereafter, referring to FIGS. 14 and 19, one of electrolyte and dielectric materials may be coated on the resulting structure, in operation S130.

For example, the electrolyte material may be an ionic liquid electrolyte or a solid electrolyte and may be formed by blending 1-Butyl-2,3-dimethylimidazolium Bis(trifluoromethanesulfonyl)imde ([EMIM][Ntf2]) and poly(vinylidene fluoride)-hexafluoroprophlene (PVDF-HFP) or by blending Nafion and poly(vinyl alcohol), but the inventive concept is not limited thereto. Similarly, even in the case of the dielectric material, the inventive concept is not limited to a specific kind of dielectric material.

Next, one of the electrolyte and dielectric materials may be dropped on the resulting structure, in which the linear source electrode 20, the linear drain electrode 30, and the linear gate electrode 40 are disposed spaced apart from and parallel to each other, and as a result, it is possible to realize a fixed disposition of the organic assembly 100 relative to the linear gate electrode 40.

Hereinafter, organic semiconductor elements according to eighth to eleventh embodiment of the inventive concept will be described with reference to the accompanying drawings.

Figure 20:
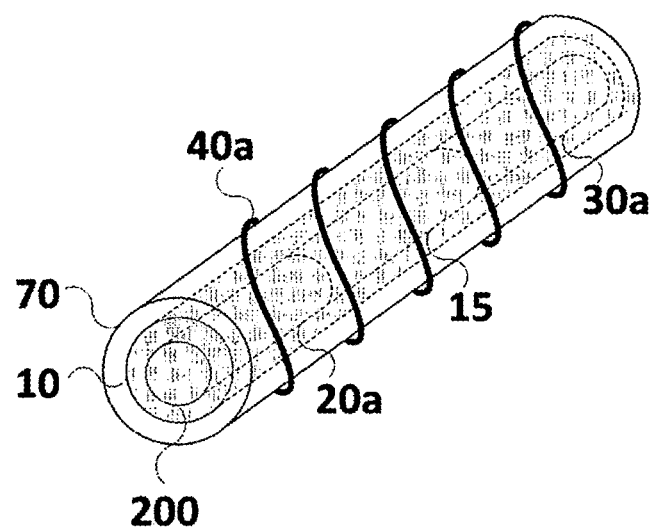
FIG. 20 is a perspective view illustrating an organic semiconductor element according to an eighth embodiment of the inventive concept.

An organic semiconductor element according to eighth embodiment of the inventive concept will be described with reference to FIG. 20. Referring to FIG. 20, a perspective view of an organic semiconductor element according to eighth embodiment of the inventive concept is illustrated.

The organic semiconductor element may include a linear fiber 200 with a source electrode pattern 20a and a drain electrode pattern 30a, an organic semiconductor layer 10, a cover layer 70, and a linear gate electrode 40a. The organic semiconductor element may be used as a sensor providing information on external environment; for example, the sensor using the organic semiconductor element may be used to detect a sensing-target material (e.g., an air pollution gas including carbon dioxide or harmful ultraviolet light), but the inventive concept is not limited thereto. For example, in the case where the organic semiconductor element of OFET type is used to detect a sensing-target material in the external environment, the presence of the sensing-target material may lead to a change in electrical characteristics of the organic semiconductor layer 10, and similarly, in the case where the organic semiconductor element of OECT type is used to detect a sensing-target material in the external environment, the presence of the sensing-target material may lead to a change in electrical characteristics of the cover layer 70 containing the electrolyte material. Such a change in the electrical characteristics of the organic semiconductor layer 10 or the cover layer 70 may lead to a change in amount or density of an electric current flowing through a channel region of the organic semiconductor layer 10 between the source electrode pattern 20a and the drain electrode pattern 30a.

The linear fiber 200 may include the source electrode pattern 20a and the drain electrode pattern 30a and may extend in the first direction. For example, the source electrode pattern 20a and the drain electrode pattern 30a may be formed on the linear fiber 200 to be spaced apart from each other in an extension direction of the linear fiber 200. Accordingly, a gap 15 may be formed between the source electrode pattern 20a and the drain electrode pattern 30a. The gap 15 may serve as a channel region of the organic semiconductor element according to the present embodiment, and the length of the gap 15 may be defined as a channel length of the organic semiconductor element. In some embodiments, the length of the gap 15 may be about 100 um, but the inventive concept is not limited thereto.

The source electrode pattern 20a and the drain electrode pattern 30a may be conductive patterns and may serve as source and drain electrodes of the organic semiconductor element. For example, the source electrode pattern 20a and the drain electrode pattern 30a may be conductive patterns formed of gold (Au) or PEDOT:PSS, but the inventive concept is not limited thereto.

The linear fiber 200 may be a linear polymer fiber formed of polymer. A portion of the linear fiber 200 formed of the polymer may be in contact with the organic semiconductor layer 10 through or at the gap 15 between the source electrode pattern 20a and the drain electrode pattern 30a.

The organic semiconductor layer 10 may include an organic semiconductor material, such as pentacene or conductive polymer materials (e.g., Poly-3-Hexylthiophene (P3HT) and PEDOT:PSS), but the inventive concept is not limited thereto.

The organic semiconductor layer 10 may be provided to enclose the linear fiber 200; that is, the linear fiber 200 may be disposed in the organic semiconductor layer 10. Accordingly, the organic semiconductor layer 10 may also extend in the first direction.

The cover layer 70 may be provided to enclose the organic semiconductor layer 10. Accordingly, the organic semiconductor layer 10 and the linear fiber 200 including the source electrode pattern 20a and the drain electrode pattern 30a may be disposed in the cover layer 70. The cover layer 70 may extend in the first direction.

The cover layer 70 may contain one of electrolyte and dielectric materials. In the case where the cover layer 70 contains an electrolyte material, the organic semiconductor element may be an OECT device, and in the case where the cover layer 70 contains a dielectric material, the organic semiconductor element may be an OFET device.

In the case where the cover layer 70 contains an electrolyte material, an external sensing-target material may affect the cover layer 70. The electrolyte material may be composed of, for example, an ionic liquid electrolyte, a solid electrolyte, or a mixture thereof, but the inventive concept is not limited thereto. Also, the electrolyte material may be formed by blending 1-Butyl-2,3-dimethylimidazolium Bis (trifluoromethanesulfonyl)imde ([EMIM][Ntf2]) and poly (vinylidene fluoride)-hexafluoroprophlene (PVDF-HFP) or blending Nafion and poly(vinyl alcohol), but the inventive concept is not limited thereto.

In the case where the cover layer 70 contains a dielectric material, an external sensing-target material may affect the organic semiconductor layer 10. Although the organic semiconductor layer 10 is provided in the cover layer 70, the external sensing-target material may pass through the cover layer 70 to reach the organic semiconductor layer 10.

The linear gate electrode 40a may be spirally wound on the cover layer 70 to face an outer surface of the cover layer 70. For example, the linear gate electrode 40a may extend to form a spirally wound structure around the cover layer 70; in other words, the linear gate electrode 40a may be wound on the cover layer 70 in such a way that its winding axis is parallel to the extension direction of the cover layer 70 or the first direction. Also, the linear gate electrode 60 may be formed of, for example, at least one of metallic materials (e.g., gold, silver, copper, and aluminum), conductive polymer materials, or carbon-based materials. For example, the linear gate electrode 40a may be provided in the form of an aluminum or gold containing wire, but the inventive concept is not limited thereto.

The organic semiconductor element, according to some embodiments of the inventive concept, may be a coiled type OECT device or a coiled type OFET device and may serve as a monofilament. The organic semiconductor element according to the present embodiment has a one-dimensional structure extending in a specific direction, and thus, it may be easily used as the mono-filament.

Figure 21:
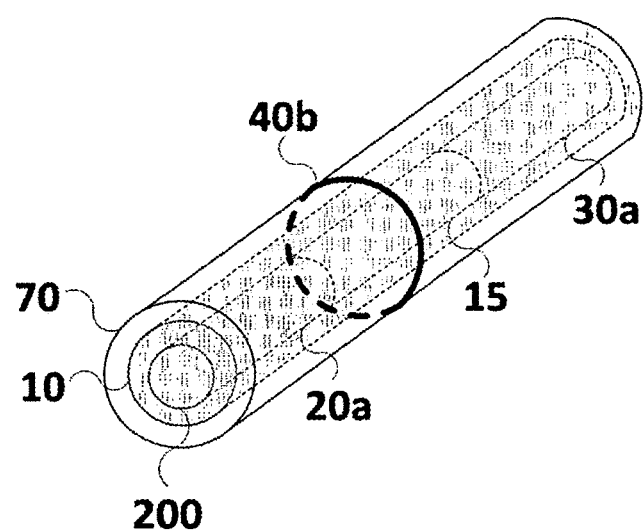
FIG. 21 is a perspective view illustrating an organic semiconductor element according to a ninth embodiment of the inventive concept.

An organic semiconductor element according to a ninth embodiment of the inventive concept will be described with reference to FIG. 21. For concise description, the following description will mainly refer to an element or feature that is different from that in the eighth embodiment or is not described therein, whereas a previously described element will be identified by a similar or identical reference number without repeating an overlapping description thereof. Referring to FIG. 21, a perspective view of the organic semiconductor element according to the ninth embodiment of the inventive concept is illustrated.

As shown in FIG. 21, in an organic semiconductor element according to the ninth embodiment of the inventive concept, the linear gate electrode 40b may be provided to have a circular shape enclosing the cover layer 70. For example, the linear gate electrode 40b may be disposed around the cover layer 70 and may be a ring-shaped structure facing the gap 15 of the linear fiber 200, but the disposition of the linear gate electrode 40b is not limited thereto.

Figure 22:
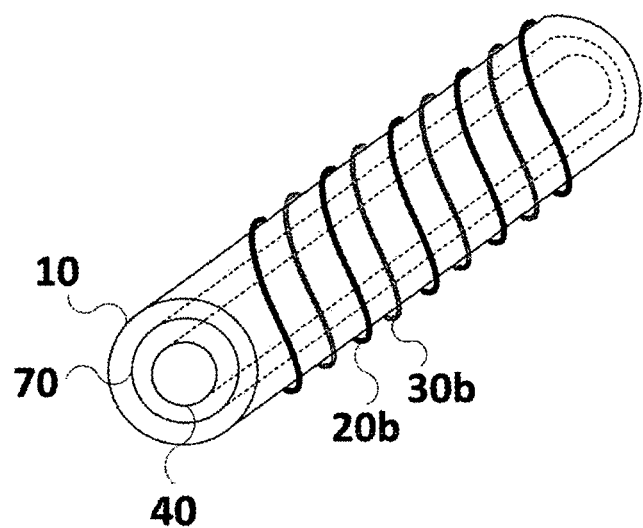
FIG. 22 is a perspective view illustrating an organic semiconductor element according to a tenth embodiment of the inventive concept.

An organic semiconductor element according to tenth embodiment of the inventive concept will be described with reference to FIG. 22. For concise description, the following description will mainly refer to an element or feature that is different from that in the eighth embodiment or is not described therein. For instance, the organic semiconductor elements according to the eighth and tenth embodiments may be different from each other, in terms of positions of the linear gate electrode, the linear source electrode, and the linear drain electrode. Referring to FIG. 22, a perspective view of an organic semiconductor element according to tenth embodiment of the inventive concept is illustrated.

An organic semiconductor element may include the linear gate electrode 40, the cover layer 70, the organic semiconductor layer 10, a linear source electrode 20b, and a linear drain electrode 30b.

The linear gate electrode 40 may extend in the first direction and may have a straight-line-shaped structure, not a coil-shaped structure.

The cover layer 70 may be provided to enclose the linear gate electrode 40, and the linear gate electrode 40 may be provided in the cover layer 70. Accordingly, the cover layer 70 may also extend in the first direction.

In the case where the cover layer 70 contains an electrolyte material, an external sensing-target material may affect the cover layer 70. Although the cover layer 70 is provided in the organic semiconductor layer 10, the external sensing-target material may pass through the organic semiconductor layer 10 to reach the cover layer 70.

The organic semiconductor layer 10 may be provided to enclose the cover layer 70, and the linear gate electrode 40 and the cover layer 70 may be provided in the organic semiconductor layer 10. The organic semiconductor layer 10 may extend in the first direction.

The linear source electrode 20b and the linear drain electrode 30b may be spirally wound on the organic semiconductor layer 10 to face an outer surface of the organic semiconductor layer 10, while maintaining a distance therebetween. For example, the linear source and drain electrodes 20b and 30b may extend to form a spirally wound structure around the organic semiconductor layer 10. In other words, the linear source and drain electrodes 20b and 30b may be wound on the organic semiconductor layer 10 in such a way that its winding axis is parallel to the extension direction of the organic semiconductor layer 10 or the first direction. Here, the linear source and drain electrodes 20b and 30b may be the spirally wound structures that are spaced apart from each other on the outer surface of the organic semiconductor layer 10, and thus, the linear source and drain electrodes 20b and 30b may not intersect or meet each other.

A distance between the linear source and drain electrodes 20b and 30b may define a channel length of the organic semiconductor element according to some embodiments of the inventive concept and may be, for example, about 100 um, but the inventive concept is not limited thereto.

The linear source electrode 20b and the linear drain electrode 30b may be linear conductive elements and may serve as source and drain electrodes, respectively, of the organic semiconductor element. The linear source electrode 20b and the linear drain electrode 30b may be formed of or include at least one of, for example, metallic materials (e.g., gold, silver, copper, and aluminum), conductive polymer materials, or carbon-based materials, but the inventive concept is not limited thereto. For example, each of the linear source and drain electrodes 20b and 30b may be provided in the form of a gold-containing wire or a polymer fiber coated with gold (Au) or PEDOT:PSS, but the inventive concept is not limited thereto. In other words, according to the organic semiconductor element in some embodiments of the inventive concept, it is possible to form the linear source and drain electrodes 20b and 30b, without any patterning process, and this may make it possible to reduce cost and time in a fabrication process.

Figure 23:
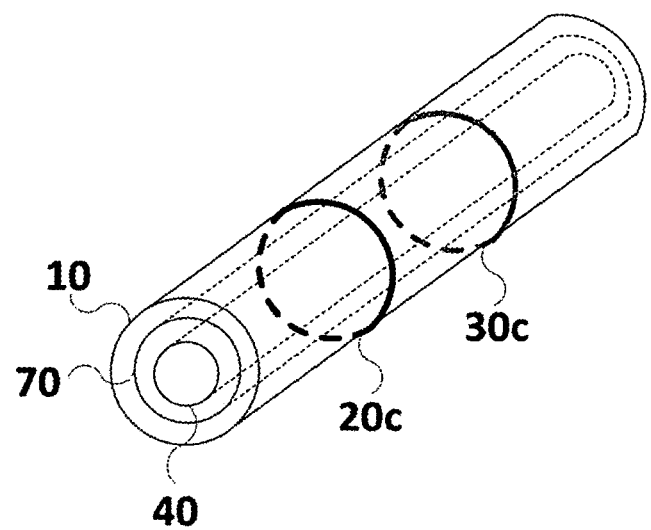
FIG. 23 is a perspective view illustrating an organic semiconductor element according to an eleventh embodiment of the inventive concept.

An organic semiconductor element according to an eleventh embodiment of the inventive concept will be described with reference to FIG. 23. For concise description, the following description will mainly refer to an element or feature that is different from that in the tenth embodiment or is not described therein, whereas a previously described element will be identified by a similar or identical reference number without repeating an overlapping description thereof. Referring to FIG. 23, a perspective view of the organic semiconductor element according to the eleventh embodiment of the inventive concept is illustrated.

As shown in FIG. 23, in an organic semiconductor element according to the eleventh embodiment of the inventive concept, the linear source and drain electrodes 20c and 30c may be provided spaced apart from and parallel to each other and each of them may have a circular shape enclosing the organic semiconductor layer 10.

Figure 24:
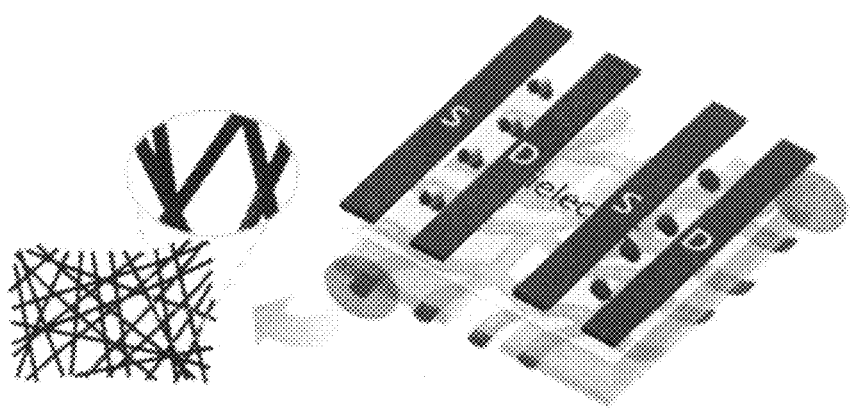
FIG. 24 is a conceptual diagram of a woven fabric structure, in which an organic semiconductor element according to some embodiments of the inventive concept is used.

Hereinafter, a woven fabric structure, in which an organic semiconductor element according to some embodiments of the inventive concept is used, will be described with reference to FIG. 24. Referring to FIG. 24, a conceptual diagram of a woven fabric structure, in which an organic semiconductor element according to some embodiments of the inventive concept is used, is illustrated.

As shown in FIG. 24, a woven fabric structure may be realized using the organic semiconductor element according to some embodiments of the inventive concept as fibers therefore. The organic semiconductor element according to some embodiments of the inventive concept may be linearly extended and may be used to fabricate a flexible fabric material, and thus, it may be used as fibers for fabricating a woven fabric structure.

In some embodiments, the organic semiconductor element according to some embodiments of the inventive concept may also be used as fibers for a non-woven fabric structure. The woven or non-woven fabric structure may be fabrics or knits having a mesh-shaped structure, a grid-shaped structure, or a non-woven structure, but the inventive concept is not limited thereto.

Figure 25:
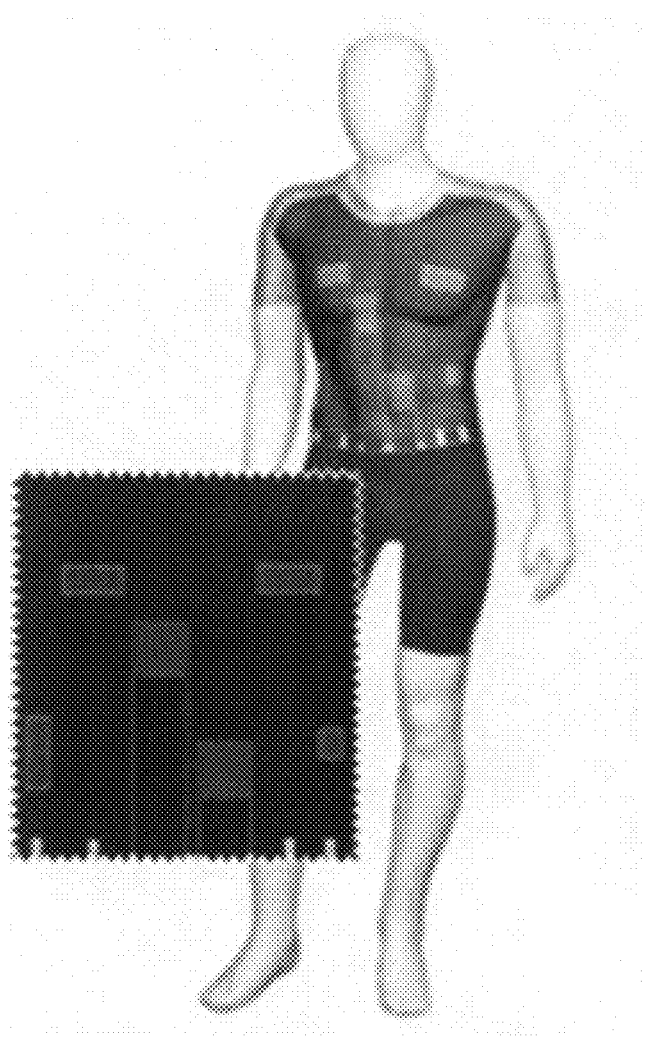
FIG. 25 is a conceptual diagram of a wearable device including an organic semiconductor element, a woven fabric structure, or a non-woven fabric structure, according to some embodiments of the inventive concept.

Hereinafter, a wearable device including an organic semiconductor element, a woven fabric structure, or a non-woven fabric structure, according to some embodiments of the inventive concept will be described with reference to FIG. 25. Referring to FIG. 25, a conceptual diagram of a wearable device including an organic semiconductor element, a woven fabric structure, or a non-woven fabric structure, according to some embodiments of the inventive concept is illustrated.

A semiconductor device according to some embodiments of the inventive concept may include at least one of the organic semiconductor element, the woven fabric structure, or the non-woven fabric structure, according to some embodiments of the inventive concept. The semiconductor device may be used to realize a sensor, a solar cell, a display device, a wearable device, and so forth, but the inventive concept is not limited thereto.

The case of the wearable device will be described as an example of various applications of the semiconductor device. The organic semiconductor element according to some embodiments of the inventive concept may serve as a sensor for detecting a sensing-target material and may be used to fabricate a woven fabric structure or a non-woven fabric structure, owing to its structural and material properties. Accordingly, in the case where the woven or non-woven fabric structure according to some embodiments of the inventive concept is used to fabricate a wearable device, a sensing-target material (e.g., an air pollution gas including carbon dioxide or harmful ultraviolet light) in external environment may be detected by the wearable device, and a user may obtain information on the presence or absence of the sensing-target material, from the wearable device. The wearable device may be fabricated in the form of, for example, clothing, but the inventive concept is not limited thereto.

According to some embodiments of the inventive concept, it is possible to form a linear source electrode and a linear drain electrode, without performing a patterning process. This makes it possible to fabricate an organic semiconductor element using a relatively simple process and consequently to reduce cost in a process of fabricating the organic semiconductor element.

According to some embodiments of the inventive concept, the organic semiconductor element can be fabricated using a simple process, and the organic semiconductor element has a structure, allowing it to be effectively used as a filament device.

While example embodiments of the inventive concepts have been particularly shown and described, it will be understood by one of ordinary skill in the art that variations in form and detail may be made therein without departing from the spirit and scope of the attached claims.

What is claimed is:

1. An organic semiconductor element, comprising:
   an organic semiconductor layer;
   a linear source electrode and a linear drain electrode provided in the organic semiconductor layer and spaced apart from and parallel to each other;
   a linear gate electrode provided on the organic semiconductor layer to cross the linear source and drain electrodes; and
   an electrolyte layer in contact with the organic semiconductor layer and the linear gate electrode,
   wherein the linear source and drain electrodes are enclosed by the organic semiconductor layer.

2. The organic semiconductor element according to claim 1,
   wherein the linear gate electrode is provided to cross a region between the linear source and drain electrodes spaced apart from and parallel to each other.

3. The organic semiconductor element according to claim 1,
   wherein the electrolyte layer comprises at least a portion interposed between the organic semiconductor layer and the linear gate electrode.

4. The organic semiconductor element according to claim 1,
   wherein the organic semiconductor layer comprises a conductive polymer material.

5. The organic semiconductor element according to claim 1,
   wherein each of the linear source and drain electrodes extend in a first direction, and
   the linear gate electrode extends in a second direction that is not parallel to the first direction.

6. The organic semiconductor element according to claim 5,
   wherein the first direction is perpendicular to the second direction.

7. The organic semiconductor element according to claim 5,
wherein the organic semiconductor layer has a top surface, on which the linear gate electrode is provided, and which extends in the first direction.

8. An organic semiconductor element, comprising:
an organic semiconductor layer;
a linear source electrode and a linear drain electrode provided in the organic semiconductor layer and spaced apart from and parallel to each other;
a linear gate electrode provided on the organic semiconductor layer to cross the linear source and drain electrodes; and
an electrolyte layer in contact with the organic semiconductor layer and the linear gate electrode,
wherein the linear source electrode comprises a plurality of linear source electrode,
the linear drain electrode comprises a plurality of linear drain electrodes, and
the plurality of linear source electrodes and the plurality of linear drain electrodes are arranged one by one in an alternate manner.

9. The organic semiconductor element according to claim 8,
wherein the plurality of linear source electrodes and the plurality of linear drain electrodes extend in a first direction,
the linear gate electrode extends in a second direction that is not parallel to the first direction, and
the plurality of linear source electrodes and the plurality of linear drain electrodes are arranged one by one in an alternate manner in the second direction.

10. A method of fabricating an organic semiconductor element, comprising:
coating a linear source electrode and a linear drain electrode, which are spaced apart from and parallel to each other, with an organic semiconductor material;
disposing a linear gate electrode to cross the linear source and drain electrodes coated with the organic semiconductor material; and
coating an electrolyte material on a resulting structure provided with the linear gate electrode.

11. The method according to claim 10,
wherein the coating of the linear source and drain electrodes with the organic semiconductor material comprises simultaneously coating the linear source and drain electrodes with the organic semiconductor material to maintain parallel separation configuration of the linear source and drain electrodes.

12. The method according to claim 10,
wherein the coating of the linear source and drain electrodes with the organic semiconductor material comprises:
providing a mold with first and second grooves, the first and second grooves extending in a first direction and parallel each other;
disposing the linear source and drain electrodes in the first and second grooves, respectively; and
coating the linear source and drain electrodes, which are provided in the first and second grooves, respectively, with the organic semiconductor material.

13. The method according to claim 12,
further comprising preliminarily coating the linear source and drain electrodes with the organic semiconductor material, before the coating of the linear source and drain electrodes with the organic semiconductor material.

* * * * *